United States Patent [19]

Malcom et al.

[11] 4,274,163
[45] Jun. 23, 1981

[54] PROSTHETIC FIXATION TECHNIQUE

[75] Inventors: Lawrence L. Malcom, San Diego; F. Richard Convery, La Jolla, both of Calif.

[73] Assignee: The Regents of the University of California, Berkeley, Calif.

[21] Appl. No.: 57,822

[22] Filed: Jul. 16, 1979

[51] Int. Cl.³ .............................................. A61F 1/00
[52] U.S. Cl. ...................................... 3/1.91; 3/1.911; 128/92 C
[58] Field of Search ........................ 3/1.91, 1.9, 1.911, 3/1, 1.912, 1.913; 128/92 R, 92 CA, 92 C

[56] References Cited

U.S. PATENT DOCUMENTS

| | | | |
|---|---|---|---|
| 3,866,248 | 2/1975 | Kummer | 3/1 |
| 3,889,665 | 6/1975 | Ling et al. | 128/92 R |
| 4,065,817 | 1/1978 | Branemark et al. | 3/1.91 |

*Primary Examiner*—Ronald Serwin

*Attorney, Agent, or Firm*—Poms, Smith, Lande & Rose

[57] ABSTRACT

In order to reduce the incidence of artificial joint failure at the interface where the prosthesis is bonded to the bone by cement, the artificial prosthesis is provided with openings, and is clamped in place to provide a peripheral seal around the end of the bone to which it is being secured. Then the cement is applied through the prosthesis under pressure, and the pressure is maintained until the cement hardens. The prosthesis may be provided with both input and output openings so that, as the cement is forced into the space between the prosthesis and the cortical bone structure, material including blood and marrow contents will be forced out the exit apertures and the pressurized cement will thereafter make good direct contact with both the bone and the prosthesis, to insure a lasting bond. The rim of the prosthesis and the matching bone surfaces may be specially prepared to provide a good pressure tight seal.

20 Claims, 8 Drawing Figures

PROSTHETIC FIXATION TECHNIQUE

BACKGROUND OF THE INVENTION

This invention relates to artificial joints, and more particularly to techniques for securing artificial joint prostheses to bones.

One serious problem which is receiving greater attention in orthopedic meetings is that of the loosening of prostheses which are employed in such artificial joints. Up to the present time, a number of techniques have been undertaken to enhance fixation. Some of the methods and apparatus which have been proposed include the use of special techniques to denude the inner cancellous bone surfaces to which the prosthesis are to be cemented, by the use of Water Pik type apparatus, bottle brushes, or hydrogen peroxide; the use of rubber dams around the opening in the bone, to facilitate the packing of cement; and the use of special arrangements similar to a "grease gun" for the injection of the cement prior to prosthesis insertion.

However, while such techniques are probably improvements over prior procedures, no substantiating data is as yet available, and it is considered probable that the results will show improvement, but that the problem of loosening of prostheses will not have been fully solved by these techniques.

A principal object of the present invention is to reduce the loosening of prostheses, by improving the bond between the prosthesis and the cement and more specially between the cement and the bone structure.

SUMMARY OF THE INVENTION

In accordance with the present invention, it has been determined that greatly improved bond strength between prostheses and the enclosing bone may be obtained by supplying the cement to the space between the prosthesis and the enclosing bone under pressure, and maintaining the pressure for a sufficient period of time to permit hardening or polymerization of the cement.

In accordance with one aspect of the invention, the prosthesis may be provided with apertures through which the cement may be supplied under pressure to the space between the prosthesis and the enclosing cancellous bone.

In addition, the periphery of the prosthesis may be provided with a rim or edge for making a tight seal with the mating surfaces of the bone, to facilitate the maintenance of elevated pressure within the space between the prosthesis and the bone so that pressure may be maintained while the cement sets.

In accordance with another feature of the invention, exit apertures may be provided through the prosthesis to permit the forcing out of blood and other substances within the intramedullary space, prior to completely filling the space between the prosthesis and the closing bone with cement, and the maintenance of high pressure within this space until the cement hardens.

Other collateral features of the technique of the invention include the preliminary placement of a plug in the central channel of the bone, to prevent undue penetration of the cement along the length of the bone when the pressurized joint is being prepared; the use of a clamp to hold the prosthesis in place while pressurized cement is being forced through it; the location of the apertures through the prosthesis on non-bearing surface areas of the prosthesis when such areas are available; the use of disposable plastic cylinders for supplying the cement, which may be somewhat more fluid than that which is conventionally employed; and the maintenance of pressures which are substantially above atmospheric pressure during the entire period of polymerization and setting up or hardening of the cement.

Advantages of the present method include significantly increased penetration and better engagement of the cement with the cancellous bone surface, as well as a decreased porosity of the solidified cement with a resultant increase in the mechanical tensile strength of that cement, and hence a greatly increased mechanical strength of the resultant interface between the artifical joint and the bone. More specifically, the average percent improvement for paired specimens, in which a comparison was made between the pressurized specimens prepared in accordance with the invention, and control specimens prepared by normal techniques were as follows: a 388% increase in fracture strength, a 198% higher shear modulus, and 420% greater energy required for fracture.

Other objects, features, and advantages of the invention will become apparent from a consideration of the following detailed description and from the accompanying drawings.

DETAILED DESCRIPTION

Before embarking on a detailed description of the drawings, it is useful to review a few of the medical terms which will be employed in the present description. Although the present invention is applicable to other types of artificial joints, it will be described in terms of a knee joint. The lower leg includes two bones, the larger of which is the tibia and the smaller bone along the outer portion of the lower leg being the fibula. The thigh or the upper leg bone is the femur. In the normal human knee joint, the lower end of the femur is provided with two rounded projections. In medical terminology a rounded projection on a bone is known as a "condyle", and one type of artificial knee joint is known as a "condylar" replacement. Various types of total knee replacement prosthesis have been used by orthopedic surgeons, and these range from relatively unconstrained models to fully constrained arrangements. A good survey article is "A Comparison of Four Models of Total Knee-Replacement Prostheses" by J.

N. Insall, M.D., et al, The Journal of Bone And Joint Surgery, Vol. 58-A, No. 6, September 1976, Pages 754 through 765. Other medical terms which may be usefully be employed in describing the present invention include the terms "distal" and "proximal" which refer to the "far", and "near" portions of the anatomy on a limb such as the leg; and with reference to the application of a prosthesis to the end of a bone, the end of the bone to which the prosthesis is being secured is referred to as the proximal end, and the other end of the bone is the distal end. Other useful medical terms include the term "cannula" which is defined as a tube for insertion into the body, and the corresponding verb "cannulate", which involves penetration with a cannula. The term "cortex" and the associated adjective "cortical" which refer to the outer layer of a body structure and with regard to bone it is the hard or dense outer portion of the bone, as compared with the inner or "cancellous" bone structure which is normally of a reticular, spongy, or lattice-like structure. Incidentally, the central portion of an elongated bone, such as the tibia, normally has a central channel or canal known as the "medulary" channel, which is free of bone and only includes marrow and other soft tissue.

Figure 1:
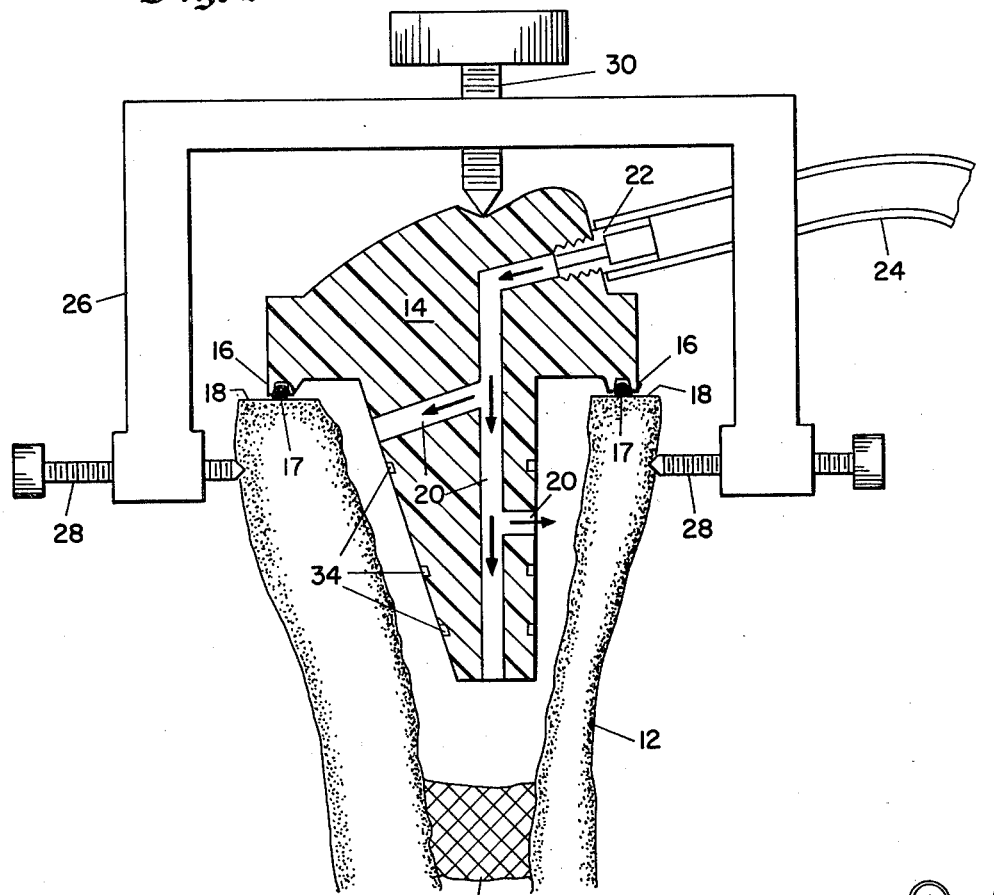
FIG. 1 is a diagrammatic showing of a prosthesis being cemented into place in the end of bone in accordance with principles of the present invention.

Now, referring to FIG. 1 of the drawings, the upper end of a tibia 12 is shown provided with an implant 14 which includes a protruding edge or lip 16 which may be provided with an O-ring 17, or other deformable gasket, and which acts to seal the implant 14 onto the surgically shaped transverse planar surface 18 of the bone. The deformable gasket should be formed of latex or other medically inert resilient material. The implant 14 includes a series of passages or multiply bifurcated cannula 20 which permit the application of medical cement to the space between the implant 14 and the inner surface of the tibia 12. The cement is supplied to the cannula 20 through the detachable threaded inlet coupling 22 and the flexible inlet tubing 24 through which the pressurized liquid medical cement is supplied.

A clamp 26 is provided with a series of threaded screws 28 which grip the superficial edge of the tibia and, through the larger hand-operated screw 30 applies a rigid fixation and immobilization force to the implant 14. This clamp 26 serves to keep the prosthesis 14 located securely and tightly on the bone surface while the space within the bone is filled with pressurized medical cement. Incidentally, shown at 32 is a plug of medical cement which had previously been inserted and hardened so that there will not be undue penetration of the pressurized cement along the length of the medulary canal when the implant 14 is being cemented into place.

Following full polymerization or hardening of the medical cement, the threaded inlet port 22 is detached by unscrewing it. The prosthesis clamp 26 is then removed from the bone and the prosthesis and the in situ pressurized fixation technique is now complete.

The medical cement which is employed is normally polymethylmethacrylate. This is available from Howmedica as "Simplex-P" and as Zimmer Bone Cement from Zimmer, and under other trade names in England and Europe. It is supplied as a mix with a liquid monomer and a powdered polymer. Following mixing of the two components there is usually about 10 minutes within which the material may be employed, before it polymerizes and hardens. In some cases, barium sulfate is added to the medical cement so that it is visible in X-ray photographs.

As mentioned above, it normally takes in the order of 10 minutes for the medical cement to fully polymerize and harden. It is a feature of the present invention that pressure is retained on the cement for this entire period of time to insure firm engagement both of the prosthesis and also of the cancellous bone which encloses it.

Referring back to FIG. 1, the implant 14 may, if desired, be provided with one or more fixation ribs or grooves 34 for locking the implant in place and for reducing the likelihood that it will be loosened.

Figure 2:
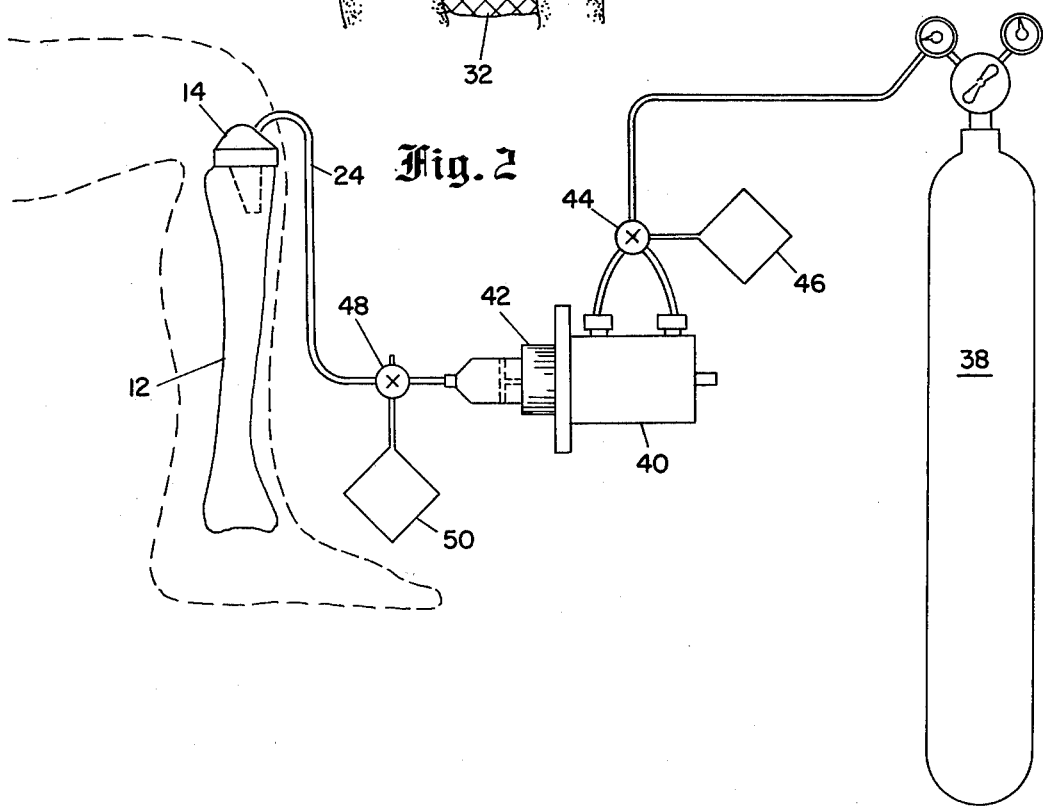
FIG. 2 is a diagrammatic showing of the complete system for supplying cement under pressure to the prosthesis of FIG. 1.

FIG. 2 is an overall schematic showing of one technique for implementing the present pressurized medical cement fixation procedure. In this example, a high pressure nitrogen gas source 38 such as is commonly found in the present day operating room, is employed to drive a pneumatically powered system, or gas pressurized piston arrangement 40. A disposable plastic cylinder 42 is filled with liquid polymethylmethacrylate, and the gas flow control valve 44 is actuated under the control of a time measuring and shut-off control arrangement 46. Connected to the flexible inlet tubing 24 at the overpressurization safety release valve 48 is a pressurization monitor and recorder 50. In connection with the showing of the implant 14 and the tibia 12, the clamp 26 as shown in FIG. 1 would of course be present, but has been omitted from FIG. 2 for simplicity.

Figure 3:
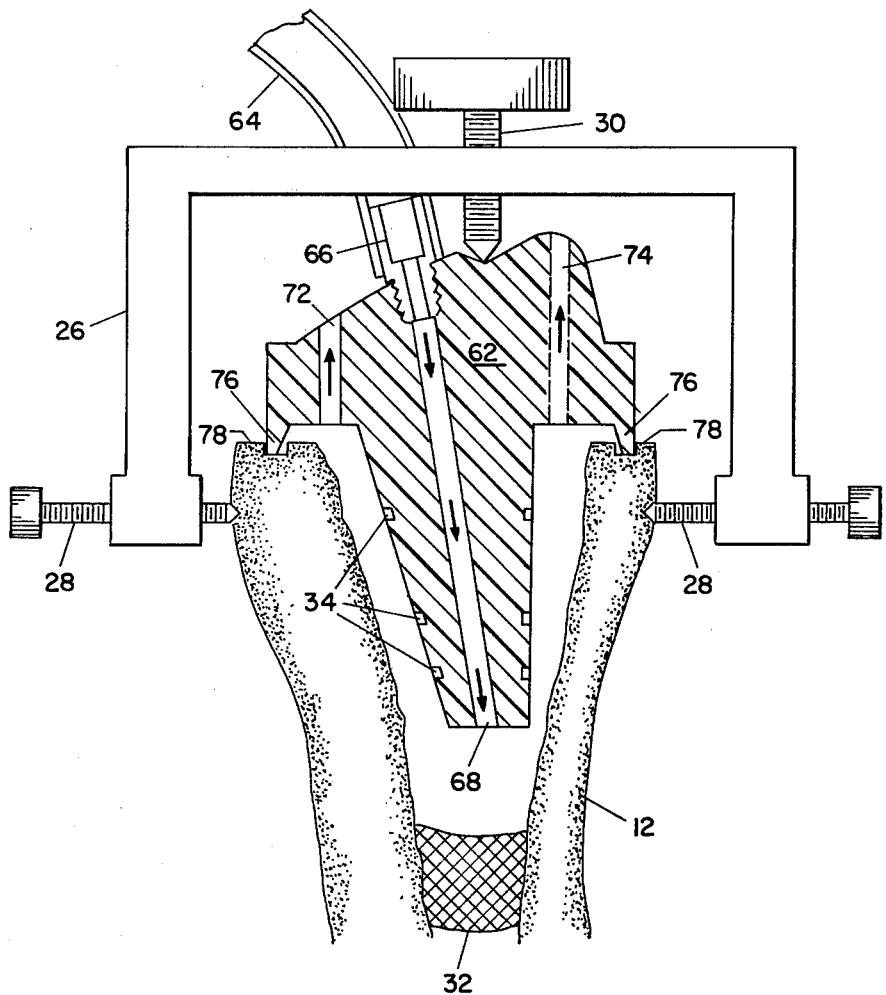
FIG. 3 shows an alternative arrangement providing separate inlet and outlet ports through the prosthesis.

FIG. 3 shows a slightly modified form of implant 62 for the implementation of the present invention. In accordance with the arrangements shown in FIG. 3, the medical cement is supplied through the flexible tubing 64 and the fitting 66 to a single cannula 68 which extends to the lower end of the implant 62. As mentioned hereinabove, there is considerable blood and other fluids which may accumulate within the recess in the end of the bone 12. In accordance with the embodiment shown in FIG. 5, the pressurized cement as it flows through the cannula 68 forces these fluids and body materials up through one or more exit cannula 72 and 74. Then, the space between the implant 62 and the inner wall of the tibia 12 is filled with cement. After all of the extraneous fluids flow through the cannula 72 and 74, and cement starts to emerge from them, they may be closed either by pressing a gloved finger over each of the holes or in any other suitable manner. In the arrangement of FIG. 3, a sharper edge 76 is shown engaging the surgically prepared proximal end 78 of the tibia 12, which may, if desired, by grooved to match the rim of the prostheses.

Figure 4:
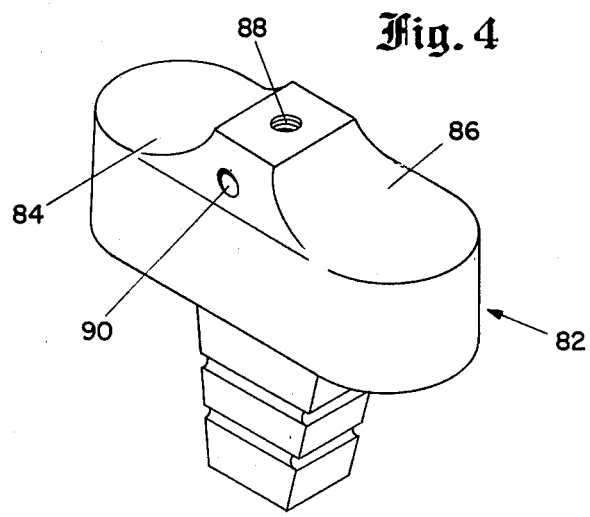
FIG. 4 is an isometric view of a knee joint prosthesis provided with inlet and outlet apertures for the implementation of the present invention.

FIG. 4 is an isometric view of a so-called duocondylar prosthesis, in which, again, an implant 82 for the tibia is shown. Between the two bearing surfaces 84 and 86, which receive the metal prosthesis which is secured to the femur, are shown the inlet opening 88, and one of the two outlet openings 90. The other outlet opening 90 is concealed behind the central ridge of the upper surface of the implant, in the showing of FIG. 4. Incidentally, it may be noted that the inlet and the outlet openings are preferably not included in the bearing surfaces 84 and 86.

Incidentally, the present orthopedic techniques for joint replacement normally involve the use of one component of medically inert stainless steel, and the other being of high density polyethylene. In the present illustrative example, the implant employed at the distal end of the tibia is of the high density polyethylene type. However, the principles of the present invention are applicable to the securing of the metal implants in place, and to implants of other materials.

Tests have been conducted relative to the present method, using unembalmed, frozen and then thawed cadaver tibias. A total condylar tibial prosthesis was cannulated and fitted with plastic tubing connected to a disposable plastic cylinder into which a pneumatic piston could be driven. The proximal tibia was prepared as for a total condylar knee replacement. A polymethylmethacrylate (PMM) plug was placed distally, as shown for example, at 32 in FIGS. 1 and 3. Liquid PMM was added to completely fill the tibial cavity, the prosthesis was inserted, clamped to the tibia, and a fixation clamp as shown at 26 in FIGS. 1 and 3 was applied. Concurrently, a second portion of the PMM medical cement was placed in the plastic cylinder attached to the pneumatic piston. Compressed nitrogen was applied to the piston which in turn pressurized the liquid PMM in the cylinder until an experimental intramedullary pressure of 100 pounds per square inch was obtained. The acrylic in the cylinder was applied under pressure through the prosthesis as the liquid polymer partially penetrated the cancellous bone, and it was maintained at 100 pounds per square inch until complete polymerization occurred. The opposite tibia was used as a control with initial plugging of the distal intramedulary canal and subsequent manual packing of the medical cement followed by the insertion by hand of a non-modified tibial implant otherwise conforming to that which was employed using the principles of the present invention.

The clamped prosthesis prevented leaking of the acrylic cement proximally. At an experimental intermedulary pressure of 100 psi, it was possible to inject up to an additional 30 cc. of cement into the already filled marrow cavity. This indicates that much lower intramedulary pressures or shorter times of pressurization might be used while still achieving adequate PMM penetration.

Figure 5B:
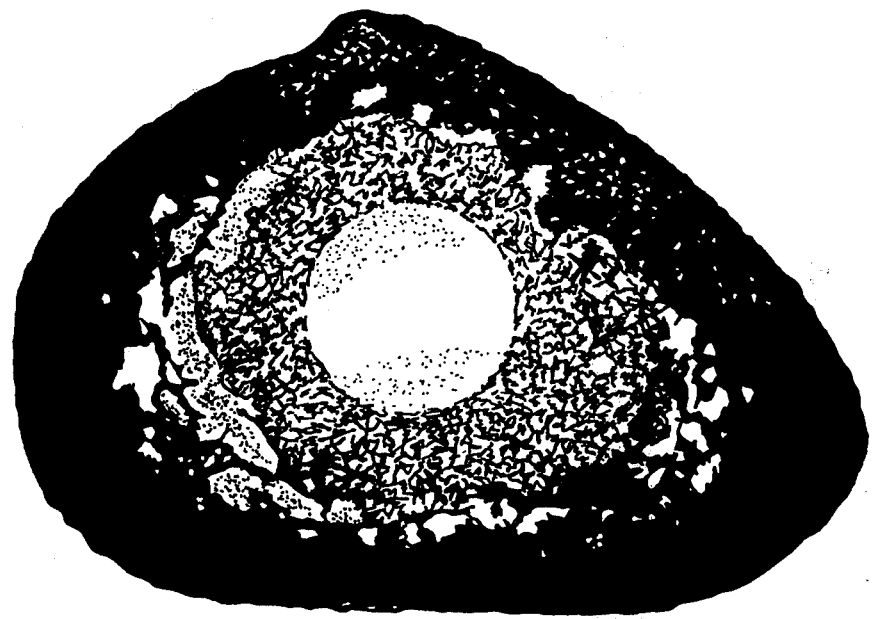
FIGS. 5A and 5B are comparative showings indicating the penetration of cement in accordance with the principles of the invention and in a control sample, respectively.
Figure 5A:
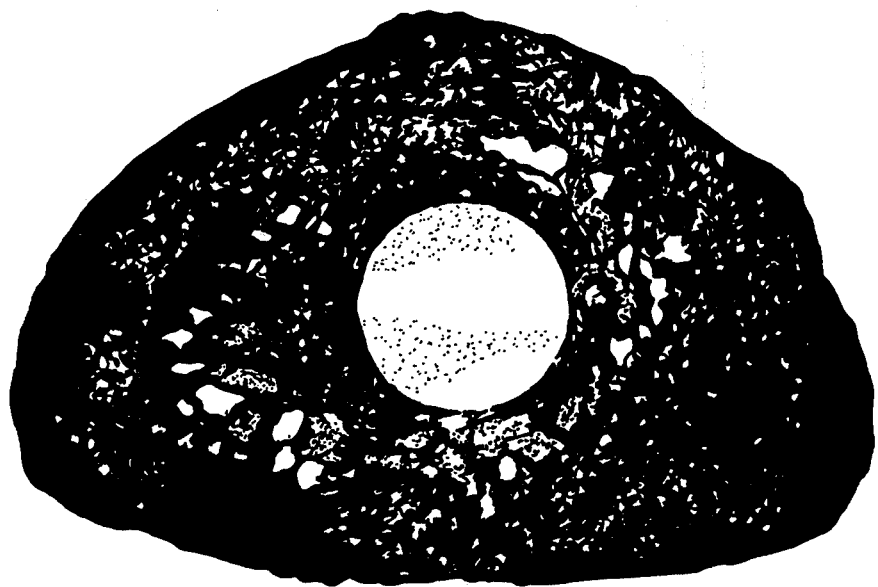
Figure 6B:
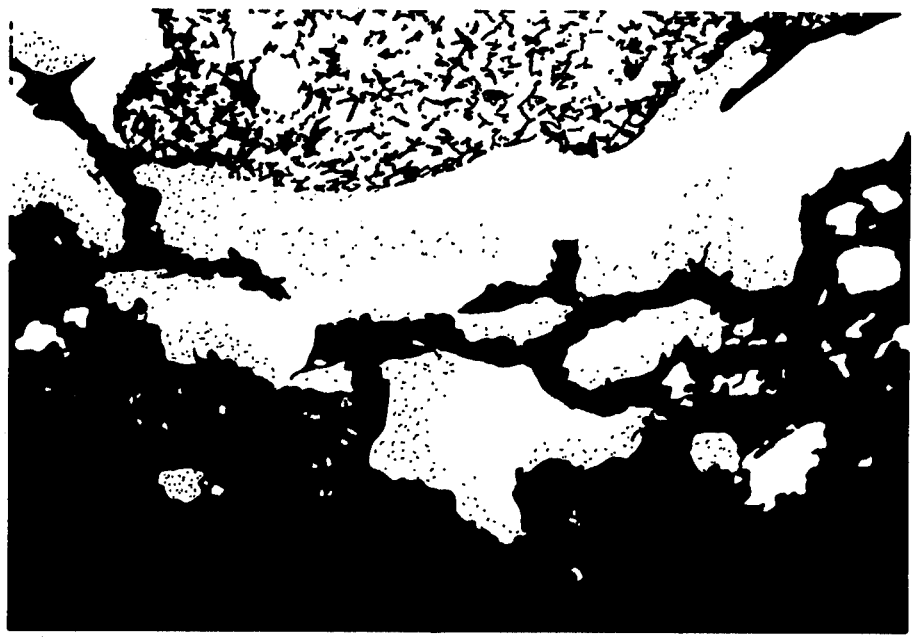
FIGS. 6A and 6B are comparative photomicrographs showing the interface between the cancellous bone and the cement for the technique of the present invention, and for the control sample, respectively.
Figure 6A:

The results of the tests are shown visually in FIGS. 5A and 5B, and in the second set identified as FIGS. 6A and 6B, with the "A" designating the pressurized sample and "B" representing the control or non-pressurized sample. FIGS. 5A and 5B are low power photomicrographs and FIGS. 6A and 6B are higher power photomicrographs showing the interface between the bone and the acrylic cement. In FIG. 5A and FIG. 5B, the central light colored circular area is a section through the stem of the high density polyethylene prosthesis, and the extended light colored areas in FIG. 5B, at the interface between the PMM and the bone indicate areas of no mechanical chemical contact. In FIGS. 6A and 6B, the photomicrographs are of different density, giving the cement and bone different appearances in the two figures, but the bone in each case is located at the bottom of the figure. With the same enlargement power being employed, the extended areas where there is little or no contact in FIG. 6B clearly show the reason for the much greater strength of the pressurized sample of FIG. 6A.

The conventional specimens from the hand-inserted side showed an average radial penetration of the PMM of 67% from the center of the intramedulary canal, while the average penetration of the pressure-injected side was 80% of the specimen radius.

Strength of materials testing of paired right and left experimental (pressurized) and control (unpressurized) specimen cross-sections were performed on a standard materials testing instrument of the type known as an "Instron Model TM-M" at a strain rate of 10 mm. per minute. In the tests, successive 1 centimeter sections were taken perpendicular to the longitudinal axis of the tibia, the bone cortex was clamped, and the central hardened PMM was mechanically shifted relative to the bone. The statistical mean or average of the results for 30 specimens are shown below in terms of the peak fracture shear stress (in Newton's per square meter), the energy to fracture (in Newton-meters), and the linear range shear modulus (in Newton's per square meter).

|  | New Technique Hydraulic pressurization | Control Hand insertion |
| --- | --- | --- |
| Fracture Shear Stress (N/m$^2$) | $4.17 \times 10^6$ | $1.55 \times 10^6$ |
| Energy to Fracture (N-m) | 1.20 | 0.59 |
| Linear Shear Modulus (N/m$^2$) | $12.1 \times 10^6$ | $4.62 \times 10^6$ |

The pressure fabricated prosthetic units consistently showed a statistically significant increase in shear stress for fracture, fracture energy, and shear stiffness. In analyzing the data, it was interesting to note that a pooled averaging of all the data, as set forth in the foregoing table, had the occasional effect of understating the advantages of the new technique. When the percentage improvement was compared on a sample by sample basis, and the percentages were averaged, however, much more surprising and dramatic results are shown. In particular, the average percent improvement for paired pressurized specimens taken from equivalent cross-sectional levels were as follows: a 388% increase in fracture strength, a 198% higher shear modulus, and 420% greater energy required for fracture (involving average ratios of 4.88, 2.98, and 5.20, respectively). Concerning the pressure to be employed in the securing of prosthesis, it was mentioned hereinabove that a (calculated) pressure of approximately 100 psi (gauge pressure) was employed. It was also noted that the penetration of the cement extended through much of the cancellous bone, approaching the very hard outer cortex of the bone. It is considered possible that somewhat lesser pressures might advantageously be employed to provide a balance between firm securing of the implant to the bone, while permitting somewhat greater flow of bodily fluids to nourish and maintain the strength of the bone.

For completeness, reference will be made to certain additional articles providing background on orthopedic procedures of the type to which the present invention relates. These articles include "Polycentric Total Knee Arthroplasty", by Dr. Matthew D. Skolnick, the Journal of Bone and Joint Surgery, September 1976, Vol. 58-A, No. 6, pages 743 through 748; and "Geometric Total Knee Arthroplasty", by Dr. Matthew D. Skolnick, The Journal of Bone and Joint Surgery, Vol. 58-A, No. 6, pages 749 through 753, September 1976. Attention is also directed to R. S. M. Ling and A. J. C. Lee, U.S. Pat. No. 3,889,665, granted June 17, 1975, which relates to an apparatus for initially inserting medical cement into an intramedulary canal, using peripheral sealing while pressurizing the cement which is being inserted. The Ling patent is apparently solely related to the initial application of cement under pressure, in the absence of the prosthesis, and it is presumed that the prosthesis is later applied to the cement manually and no pressure is employed to seal the implant to the previously located cement, nor is pressure applied while the medical cement is hardening.

In closing, it is noted that the present invention has been described and illustrated in connection with a tibial prosthesis. However, the principles disclosed herein are clearly applicable to other types of artificial joints, such as hip and shoulder joint prostheses, by way of specific example, and to the pressurized cementing of prostheses for such other joints to insure a firm bond. Also, instead of the specific apparatus disclosed herein, other arrangements may be provided for supplying the liquid cement and for holding and sealing the prosthesis in place while the pressurized medical cement is being applied. Accordingly, the present invention is not to be limited to that precisely as shown and disclosed herein.

What is claimed is:

1. A method for securing an implant to a bone comprising the steps of:
   sealing the implant to the bone to form an enclosed space between the implant and the bone; and
   providing a source of medical cement at high pressure;
   supplying medical cement at high pressure from said source through a closed channel to the space between the implant and the bone; and
   maintaining the medical cement under pressure while the medical cement solidifies.

2. A method as set forth in claim 1 including the step of supplying said medical cement through a closed path extending through said implant.

3. A method as defined in claim 1 comprising the additional step of mechanically clamping said implant to the bone prior to applying pressurized medical cement thereto.

4. A method as defined in claim 1 comprising the additional step of plugging the distal portion of said bone with medical cement and permitting it to harden prior to the application of additional pressurized cement.

5. A method as defined in claim 1 comprising the additional steps of providing both input and output cannula through said implant, and of closing said output cannula after other fluids stop flowing through said output cannula and said medical cement appears at the exposed openings of the output cannula.

6. A method as defined in claim 1 including the steps of removing material from one end of a bone to receive an implant in the form of an artificial joint prosthesis.

7. A method as defined in claim 1 including the step of providing a recess in the end of a bone, and supplying an initial quantity of medical cement to said recess prior to sealing said implant to said bone and extending into said recess.

8. An implant for securing to a bone comprising:
   a medically inert joint prosthesis including a surface for cementing to the inside of a bone, and an outer joint bearing surface;
   means including at least one cannula having a length which is substantially greater than its diameter extending through said prosthesis from one of said surfaces to the other, for supplying medical cement under pressure to the interface between said prosthesis and the inner surface of the bone; and
   said prosthesis including means at one end of said cannula for making sealing engagement with an external conduit to be utilized in supplying said medical cement.

9. An implant as defined in claim 8 further comprising a peripheral lip on said prosthesis extending toward the desired contact area between said prosthesis and the bone to seal the space between the prosthesis and the bone.

10. An implant as defined in claim 8 wherein the outer portion of said cannula is threaded to receive a fitting to supply the medical cement.

11. An implant as defined in claim 8 wherein said cannula is bifurcated to direct the cement to several zones between the prosthesis and the bone.

12. An implant as defined in claim 8 wherein at least one additional exit cannula is provided, and wherein said cannula for supplying medical cement is of significantly greater length than said exit cannula.

13. An apparatus for cementing implants to bones under pressure comprising:
   a medically inert implant having at least one cannula extending through it;
   clamping means for securing said implant to a bone;
   a source of medical cement under high pressure;
   a conduit connected from said source to said cannula; and
   means for supplying medical cement from said source through said conduit and through said cannula to the space between said implant and said bone while they are clamped together.

14. An apparatus as defined in claim 13 including disposable piston apparatus for supplying medical cement to said implant.

15. An apparatus as defined in claim 13, and including peripheral means for sealing said implant to said bone.

16. A method for fixing a joint prosthesis onto a long bone comprising the steps of:
   forming a cavity in one end of the bone;
   holding a joint prosthesis having a cement injection cannula extending through it onto said bone and extending into said cavity;
   providing a source of liquid cementing material under high pressure;
   attaching a conduit between said source of high pressure material and said cannula;
   injecting liquid cementing material under pressure from said source through said conduit and through the prosthesis and into said cavity; and
   maintaining the cementing material under pressure until the cementing liquid hardens into solid cement.

17. A medically inert implantable prosthesis including a solid body portion, a cannula having a length many times its diameter extending through said solid body portion; and having means including a port at one end of said cannula for sealing engagement with an external conduit for injecting medical cement through said port, and additional channel means in said prosthesis connected to receive said cement following flow through said port for controlling the flow of said cement.

18. A method as defined in claim 1 further comprising the step of externally controlling the pressure of said medical cement during hardening.

19. A method as defined in claim 18 further comprising externally maintaining the pressure of said cement substantially constant during hardening.

20. An implant as defined in claim 8 comprising resilient deformable gasket means for sealing the periphery of said joint prosthesis to said bone.

* * * * *